United States Patent [19]

Bezoari

[11] Patent Number: 4,864,047

[45] Date of Patent: Sep. 5, 1989

[54] AMINOPHENOXYPHOSPHAZENES AND PROCESS FOR PRODUCING SAME

[75] Inventor: Massimo D. Bezoari, Baton Rouge, La.

[73] Assignee: The Dow Chemical Company, Midland, Mich.

[21] Appl. No.: 137,552

[22] Filed: Dec. 23, 1987

Related U.S. Application Data

[63] Continuation-in-part of Ser. No. 912,465, Sep. 29, 1986, abandoned.

[51] Int. Cl.$^4$ ............................................. C07H 9/14
[52] U.S. Cl. .................................................... 558/80
[58] Field of Search .......................................... 558/80

[56] References Cited

U.S. PATENT DOCUMENTS

| | | | |
|---|---|---|---|
| 3,206,494 | 9/1965 | Lund et al. | 558/80 |
| 3,240,723 | 3/1966 | Lund | 558/80 |
| 3,446,876 | 5/1969 | Breslow | 558/80 |
| 4,029,634 | 6/1977 | Meredith | 260/45.9 NP |
| 4,107,108 | 8/1978 | Dieck et al. | 521/85 |
| 4,117,041 | 9/1978 | Guschl | 558/80 |
| 4,124,557 | 11/1978 | Dieck et al. | 521/90 |
| 4,179,555 | 12/1979 | Cheng et al. | 528/168 |
| 4,440,921 | 4/1984 | Allcock et al. | 558/168 |

OTHER PUBLICATIONS

Kumar, Devendra, et al., Journal of Polymer Science: Polymer Chemistry Edition, vol. 22, John Wiley & Sons, Inc. (1984), pp. 927-943.

Kumar, Devendra, Journal of Polymer Science: Polymer Chemistry Edition, vol. 23, John Wiley & Sons, Inc. (1985), pp. 1661-1670.

Kajiwara et al., "Phosphonitrilic Chloride: 23".

*Primary Examiner*—Anton H. Sutto
*Attorney, Agent, or Firm*—J. M. Pelton; D. R. Howard; R. G. Waterman

[57] ABSTRACT

This invention relates to a process for preparing compounds of the formula, $$N_3P_3(R_1)_n(R_2)_{6-n}$$

wherein $R_1$ is an aminophenoxide; $R_2$ has up to 6 carbon atoms and is an alkoxy, an alkenoxy, a fluoro-substituted alkoxy, a fluoro-substituted alkenoxy or an aryloxy radical; and n is a whole integer $\geq 1$ and $\leq 6$. The process comprises reacting a chlorocyclotriphosphazene with an $R_1$ salt to form an $R_1$-chlorocyclotriphosphazene which is further reacted with an $R_2$ salt.

Novel compounds of the formula, $$N_3P_3(R_1)_nCl_{6-n}$$

are also disclosed.

11 Claims, No Drawings

AMINOPHENOXYPHOSPHAZENES AND PROCESS FOR PRODUCING SAME

CROSS-REFERENCE TO RELATED APPLICATION

This Application is a continuation-in-part of my co-pending application Ser. No. 912,465, filed Sept. 29, 1986, now abandoned.

BACKGROUND OF THE INVENTION

This invention relates to a process for producing alkoxy-, alkenoxy-, fluoro-substituted alkoxy-, fluoro-substituted alkenoxy- and aryloxy- aminophenoxycyclotriphosphazenes. This invention also relates to aminophenoxychlorocyclotriphosphazenes which are used as intermediates in the subject process.

It is reported by Kumar et al. in "High-Strength Fire- and Heat-Resistant Imide Resins Containing Cyclotriphosphazene and Hexafluoroisopropylidene Groups", *Journal of Polymer Science*, Volume 22, pages 927–943 (1984), John Wiley & Sons, Inc., that triphenoxy-tris-(aminophenoxy)cyclotriphosphazenes are used as intermediates to produce maleimidophenoxycyclotriphosphazenes which are linked by hexafluoroisopropylidenediphthalimide groups to yield high strength, fire- and heat- resistant polymers. In "Polybismaleimide Containing Tetrakisphenoxycyclotriphosphazenes", D. Kumar, *Journal of Polymer Science*, Volume 23, pages 1661–1670 (1985), John Wiley & Sons, Inc., it is reported that tetraphenoxy-bis-(aminophenoxy)cyclotriphosphazene is an intermediate used in the production of tetraphenoxy-bis-maleimidocyclotriphosphazene which is polymerizable to produce a heat-resistant polymer. The processes described for producing triphenoxytris(aminophenoxy)cyclotriphosphazene and tetraphenoxybis(aminophenoxy)cyclotriphosphazenes require at least three steps and involve, first, reacting hexachlorocyclotriphosphazene with sodium phenoxide to form triphenoxy-trichlorocyclotriphosphazene, in the case of synthesizing the former, and tetraphenoxydichlorocyclotriphosphazene, in the case of synthesizing the latter, and then with sodium nitrophenoxide. The resultant products are, respectively, triphenoxytris(nitrophenoxy)cyclotriphosphazene and tetraphenoxybis(nitrophenoxy)cyclotriphosphazene.

These products are then subjected to catalytic hydrogenation by contacting same with a catalyst, such as platinum oxide, in the presence of hydrogen gas. While these processes achieve their intended purpose, they are disadvantaged in that they are multi-stepped, require an expensive catalyst and use an explosive gas, i.e., hydrogen.

Not only are the above phenoxyaminophenoxycyclotriphosphazene compounds useful as intermediates, but it has also been found that they exhibit flame-retardant properties in flexible foam compositions. One disadvantage of flame retardants commonly used with polymeric materials is that they contain significant amounts of chlorine and/or bromine, which are evolved as gaseous hydrogen chloride and hydrogen bromide under fire conditions. The toxicity of hydrogen chloride and hydrogen bromide makes the use of such flame retardants less than desirable especially in those cases where people are expected to be present in a closed area, such as an airplane, theater, etc. Further, many present day flame retardants are present in the polymer formulation as an additive and are, thus, not bonded to the polymer. Without polymer bonding, the flame retardant has a tendency, over a period of time, to leach out of the polymeric material thereby decreasing its flame retardant properties, and causing possible toxicity hazards.

The use of aminophenoxyphosphazenes as flame retardants in a polymeric formulation avoids both the problem of hydrogen chloride and hydrogen bromide generation and the problem of flame retardant leaching. The former problem is diminished as the aminophenoxyphosphazene can be selected to contain little or no chlorine and bromine while the latter problem is greatly reduced as the aminophenoxyphosphazene copolymerizes, via its aminophenoxy functional groups, with the polymeric material.

Because of the value of such aminophenoxyphosphazenes, it is desirable that an efficient, simple process be made available for their manufacture.

It is therefore an object of this invention to provide a noncatalytic, two-step process for the production of alkoxy-, alkenoxy-, fluoro-substituted alkoxy-, fluoro-substituted alkenoxy- and aryloxyaminophenoxycyclotriphosphazenes, which process does not require the use of hydrogen gas. It is a further object of this invention to provide novel intermediates useful in the foregoing process. Another object of this invention is the provision of a novel process for producing hexaaminophenoxyphosphazene.

THE INVENTION

This invention relates to a process for the production of aminophenoxycyclotriphosphazenes of the formula:

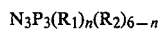

wherein $R_1$ is an aminophenoxy radical of the formula,

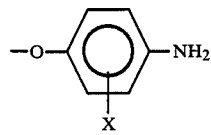

and $R_2$ has up to 6 carbon atoms and is an alkoxy, an alkenoxy, a fluoro-substituted alkoxy, a fluoro-substituted alkenoxy or an aryloxy radical of the formula,

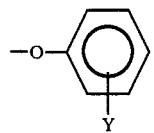

wherein each X is independently selected for each aminophenoxy radical from Cl, Br, F and H, each Y is independently selected for each aryloxy radical from Cl, Br, F and H, and wherein n is a whole integer which is $\geq 1$ and $\leq 6$. Since each X and Y are independently selected for, respectively, each aminophenoxy and aryloxy radical, $R_1$ and $R_2$ can each represent different radical combinations. For example, $R_1$ can represent the combination of (2-chloro-3-aminophenoxy)-di(aminophenoxy). Similarly, $R_2$ can represent the combination, as an example, diphenoxy-(4-chlorophenoxy)-(3-bromophenoxy).

The process comprises reacting a chlorocyclotriphosphazene and an $R_1$ salt to form an $R_1$-chlorocyclotriphosphazene having n $R_1$ substitutents and (6−n) chloride substituents, and then reacting the $R_1$-chlorocyclotriphosphazene with an $R_2$ salt for a time period sufficient to yield the desired $R_1$-$R_2$-cyclotriphosphazene. The reaction occurs in the presence of an inert, organic solvent medium and at a temperature within the range of from about 20° C. to about 150° C. The molar ratio of the chlorocyclotriphosphazene to the $R_1$ salt is from 1:1 to 1:6 depending on the degree of substitution desired. The molar ratio of the $R_1$-chlorocyclotriphosphazene reactant to the $R_2$ anion component of the $R_2$ salt is 1:b wherein b>5−n. Improved yields—indeed, yields up to 100%—can be achieved if b≧6−n. (The yield is based upon NMR analysis of the reaction mix.)

The subject process may be represented by:

$(NPCl_2)_3 + (n/k)M(R_1)_k \rightarrow N_3P_3(R_1)_nCl_{6-n} + MCl_k$  (I)(a)

$N_3P_3(R_1)_nCl_{6-n} + (a/k)M(R_2)_k \rightarrow N_3P_3(R_1)_n(R_2)_{6-n} + MCl_k$  (b)

wherein $R_1$, $R_2$ and n are as previously described; a is greater than 5−n; M is an inorganic cation, preferably a metal, such as Na, K, Li, Ca, Mg, and the like; and k is the oxidation state of M and is 1 or 2.

This invention also relates to intermediates used in the process of this invention. These intermediates have the formula:

$N_3P_3(R_1)_nCl_{6-n}$ wherein $R_1$ and n are as previously described.

This invention also relates to a process for preparing $N_3P_3(R_1)_6$ wherein $R_1$ is as previously defined. The process comprises reacting hexachlorocyclotriphosphazene with an $R_1$ salt at a temperature within the range of from about 0° C. to about 150° C. in the presence of an inert organic solvent. This process may be represented by:

$N_3P_3Cl_6 + 6/kM(R_1)_k \rightarrow N_3P_3(R_1)_6$  (II)

wherein k, M and $R_1$ are as previously defined. The molar ratio of hexachlorocyclotriphosphazene to the $R_1$ anion is preferably 1:r, wherein r>5, preferably.

For both processes of this invention, i.e., reactions I(a) and (b) and II, the particular inert organic solvent used is not critical. The solvent need only be inert in the reaction system and be capable of solubilizing the reactants under reaction conditions. For example, solvents such as octane, heptane, hexane, cyclohexane, benzene, toluene, xylene, diglyme, triglyme, tetraglyme, tetrahydrofuran, dioxane, and mixtures thereof, are all suitable. To achieve convenient temperature control, the processes of this invention are preferably run at reflux conditions and, thus, in these preferred cases, the solvent used is one which will provide reflux at the chosen process temperature. A preferred solvent is tetrahydrofuran as it provides good solubility and reflux at a temperature of from about 60° C. to about 70° C.

Process (I) is generally run within the temperature range of from about 50° C. to about 140° C. High yields are obtained when the process temperature is within the range of from about 60° C. to about 70° C. Temperatures substantially lower than 50° C., e.g., 0° C., may very well produce the $R_1$-$R_2$-cyclotriphosphazene product sought; however, the yield is predicted to be low and reaction times long. Temperatures much in excess of 140° C. are not desirable as it is expected that some inter- and intra- molecular cross-linking will occur. Such cross-linking lowers the yield of the product. When temperatures above 70° C. are used, it is preferred that the process be initiated at a lower temperature, say about 20° C. to about 50° C., followed by the raising of the temperature up to the selected level. By providing such a temperature profile over process time, the formation, during the initial phase of the process, of undesirable cross-linked products is avoided.

The reaction time for process (I) should be sufficiently long to achieve the desired $R_1$ substitution of chloride in the chlorocyclotriphosphazene and then $R_2$ substitution of the chloride constituents present in the $R_1$-chlorocyclotriphosphazene reactant. The rate of chloride substitution is interrelated with process temperature. After process initiation, the higher the temperature used, the shorter the reaction period will be. Generally speaking, for the temperature range of 50° C. to 140° C., the reaction period will be about 200 hours for the lower end of the range to about 50 hours for the upper end of the range. For the temperature range of 60° C. to 70° C., the reaction period will be within the range of from about 170 hours to about 70 hours.

While process (I) is preferably run under reflux conditions, it is to be understood that reflux conditions need not be used, but instead, can be replaced by other temperature control techniques, such as by reactor immersion in a controlled temperature bath.

The order of addition of the $R_1$-chlorocyclotriphosphazene and $R_2$ salt reactants is not critical. However, agitation, e.g., stirring is useful in ensuring uniformity of reactant concentrations in the reaction mix.

The determination of a minimum molar ratio of the $R_1$-chlorocyclotriphosphazene to the $R_2$ anion component of the $R_2$ salt is dependent upon the chloride content of the former. As there are 6−n chlorides in the phosphazene reactant, the minimum molar ratio of phosphazene reactant to $R_2$ anion needed to give some yield of the $R_1$-$R_2$-cyclotriphosphazene product is 1:b wherein b≧5−n. Since reaction yield is determinative of process efficiency, the value of b=6−n, the minimum amount of $R_2$ radicals needed to replace all of the chlorides in the phosphazene reactant, is preferred. Generally, a slight molar excess, say, 1 mole percent to about 10 mole percent, of $R_2$ anion will be used to ensure complete chloride substitution. Molar ratios in which 6−n>b>5−n can be used to produce mixes of partially chloride substituted and completely chloride substituted product. Such mixes may provide the property sought and thus, in these cases, further chloride substitution may not represent a correct economical choice.

As before noted, $R_2$ has up to 6 carbon atoms and is an alkoxy, an alkenoxy, a fluoro-substituted alkoxy, a fluoro-substituted alkenoxy radical or an aryloxy radical of the above specified formula. Exemplary of $R_2$ are the radicals: methoxy; ethoxy; isopropoxy; butoxy; ethenoxy; butanoxy; pentanoxy; hexanoxy; 2-fluoroethoxy; 2,2,2-trifluoroethoxy; 2,2,3,3,4,4,4-heptafluorobutoxy; 2,3,3,4,4,4-hexafluoro-1-butenoxy; 3,5,5-trifluoro-1-pentoxy; phenoxy; p-chlorophenoxy; o-chlorophenoxy; m-bromophenoxy; p-fluorophenoxy;

m-chlorophenoxy; and the like. Generally, the lower the carbon content of the radical, the more preferred it is from a fire retardant standpoint as there is less carbon available as fuel.

The aminophenoxy radical, $R_1$, is exemplified by: p-aminophenoxy; m-chloro-p-aminophenoxy; o-chloro-p-aminophenoxy; m-fluoro-p-aminophenoxy; o-bromo-p-aminophenoxy; and the like.

The $R_1$-$R_2$-cyclotriphosphazene product of process (I) can have any of the several $R_1$ and $R_2$ combinations which are in keeping with the allowable values of n. For example, the products can be: triphenoxy-tris(aminophenoxy)cyclotriphosphazene; tetraphenoxy-bis(aminophenoxy)cyclotriphosphazene; monophenoxy-penta(aminophenoxy)cyclotriphosphazene; triisopropoxy-tris(o-chloro-p-aminophenoxy)cyclotriphosphazene; bis(2,2,3,3,4,4,4-heptafluorobutoxy)-tetra(aminophenoxy)cyclotriphosphazene; tris(2,2,2-trifluoroethoxy)-tris(aminophenoxy)-cyclotriphosphazene; tetra(2,2,3,3,4,4,4-heptafluorobutoxy)-bis(aminophenoxy)-cyclotriphosphazene; mono(3,5,5-trifluoropentoxy)-penta(o-chloro-p-aminophenoxy)cyclotriphosphazene; tris(1,2,3,4,4,4-hexafluoro-2-butenoxy)-tris(m-fluoro-p-aminophenoxy)cyclotriphosphazene; penta(o-chlorophenoxy)-mono(aminophenoxy)cyclotriphosphazene; tetra-(m-bromo-phenoxy)-bis(o-chloro-p-aminophenoxy)cyclotriphosphazene; and the like.

As indicated above, the $R_1$ salt has the formula:

$$M(R_1)_k$$

wherein $R_1$, M and k are previously defined. Exemplary of suitable salts are sodium aminophenoxide, potassium aminophenoxide, lithium aminophenoxide, magnesium aminophenoxide and calcium aminophenoxide. Most highly preferred is sodium aminophenoxide.

The $R_1$ salt is simply prepared by reaction of aminophenol with a base, such as NaH, to yield the salt and water or hydrogen.

As is seen above, the $R_2$ salt reactant has the formula:

$$M(R_2)_k$$

wherein $R_2$, M and k are as previously described. Exemplary of suitable salts are: sodium phenoxide, potassium phenoxide; sodium butenoxide; calcium isopropoxide; sodium 2,2,2-trifluoroethoxide; magnesium 2,2,3,3,4,4,4-heptafluoro-butoxide; lithium 3,5,5-trifluoro-pentoxide; potassium p-chlorophenoxide; sodium-m-fluorophenoxide; and the like. Most highly preferred salts are the sodium salts.

The $R_2$ salt is conveniently prepared by the reaction of $R_2$H with a base, such as NaH, to yield the salt and water or hydrogen. The salt can also be purchased commercially. For example, the isopropoxide salt can be purchased from Morton Thiokol (Alfa), Inc.

As shown above, the $R_1$-chlorocyclotriphosphazene reactant has the formula:

$$N_3P_3(R_1)_nCl_{6-n}$$

wherein $R_1$ and n are defined as above. This reactant can be conveniently prepared in accordance with the following reaction:

$$(NPCl_2)_3 + (n/k)M(R_1)_k \rightarrow N_3P_3(R_1)_nCl_{6-n} + MCl_k \quad \text{I(a)}$$

wherein n, M, k and $R_1$ are as defined previously. The reaction occurs at a temperature within the range of from about 0° C. to about 150° C. and in the presence of an inert organic solvent. A preferred temperature range is from about 20° C. to about 70° C. The $MCl_k$ salt will form a precipitate and can be filtered from the reaction mix. To ensure that the hexachlorocyclotriphosphazene is not subjected to a molar ratio of hexachlorocyclotriphosphazene to the $R_1$ anion component of the $R_1$ salt greater than 1:n, the $R_1$ salt is added slowly to the reaction mix with the reaction mix being continuously agitated, such as by stirring. The reaction is preferably initiated at a temperature at the lower end of this preferred temperature range and then brought up to reflux temperature which is at the upper end of this range. The initiation temperature is dependent upon the value of n. The larger the n value, the higher the initiation temperature. Thus, when n is 2 or 3, the reagents are combined at 20° C. to about 25° C. The total reaction time can vary between about 3 hours to about 172 hours, depending on the value of n. For example, when n is 2 or 3, and the initiation reaction temperature is between about 20° C. and about 25° C., and the reflux temperature attained by the exotherm is about 70° C., the preferred reaction time is 3 to about 10 hours, without external application of heat.

Suitable $R_1$-chlorocyclophosphazene reactants are: aminophenoxy-pentachlorocyclotriphosphazene; tris(o-chloro-p-aminophenoxy)-trichlorocyclotriphosphazene; tris(aminophenoxy)-trichlorocyclotriphosphazene; tris(o-bromo-p-aminophenoxy)-trichlorocyclotriphosphazene; tetra(aminophenoxy)-dichlorocyclotriphosphazene; and bis(aminophenoxy)-tetrachlorocyclotriphosphazene. Other suitable salts are selected depending upon the identity of $R_1$ and the value of n.

The $R_1$ salt reactant can be prepared in accordance with the reaction:

$$R_1H + MH_k \rightarrow M(R_1)_k + H_2$$

$R_1H$ represents an aminophenol, be it substituted or unsubstituted, in accordance with the identity of X. This reaction occurs in an inert organic solvent, which solvent is preferably the same solvent which is used in the $R_1$-chlorocyclotriphosphazene/$R_2$ salt reaction. The reaction mix should be agitated, e.g., stirred, and is preferably heated to reflux. The order of addition of the reactants is not critical. The reaction temperature is within the range of from about 0° C. to about 150° C. and the reaction runs for that period of time necessary to ensure complete reaction of the $R_1H$ reactant. Such reaction time is preferably from about 0.5 hours to about 24 hours. The base should be at least equimolar to the aminophenol reactant and is preferably used in excess. Such a molar ratio between the base and the aminophenol is essential because, if there is any aminophenol contamination of the $R_1$ salt, the aminophenol presence results in the production of aminol derivatives of chlorocyclotriphosphazene rather than the desired $R_1$ derivatives. This is believed to be due to the faster rate of reaction between aminophenol and $(NPCl_2)_3$ than is the case for the $R_1$ salt. Even further, formation of the aminol derivative results in acid production which neutralizes the $R_1$ salt and results in production of even more aminophenol.

Process (II) occurs at a temperature within the range of from about 0° to about 150° C. in the presence of the before described inert organic solvents. A preferred temperature range is from about 20° C. to about 150° C. The order of addition of the hexachlorocyclotriphosphazene and of the $R_1$ salt is not critical, but addition of the phosphazene to the $R_1$ salt is preferred. During the addition of the two reactants, the resultant reaction mix is preferably continuously agitated, such as by stirring. The $MCl_k$ salt by-product will form as a precipitate and can be filtered from the reaction mix. The total reaction time can vary between about 3 hours to about 172 hours. A preferred total reaction time is from about 36 to about 120 hours.

The following examples are submitted for the purpose of further illustrating the nature of the present invention and are not to be construed as a limitation on the scope thereof.

The NMR spectroscopy used in analyzing the reaction products in various of the following Examples was 31P NMR spectroscopy. In general, the instrument, a JEOL 90X FT NMR, was locked onto acetone-d6, and the shift of 85% $H_3PO_4$ set to zero. Samples were analyzed in THF solution with a coaxial tube containing acetone-d6.

All spectra exhibited AB2 systems, the appearance of which varies, depending on the ratio of coupling constant, J, to chemical shift difference, v, as described in "Applications of Nuclear Magnetic Resonance Spectroscopy in Organic Chemistry," L. J. Jackman, S. Sternhell, Pergamon Press, London, 1969, pp. 130–132; "Organic Spectroscopy—An Introduction," S. F. Dyke, A. J. Floyd, M. Sainsbury, R. S. Theobald, Penguin, England, 1971, pp. 120–122; and "Nuclear Magnetic Resonance," W. W. Paudler, Allyn and Bacon, Boston, 1971, pp. 115–120. The chemical shifts gave good correlation with shifts reported for similar aminophosphazenes in "Phosphorus-Nitrogen Compounds," H. R. Allcock; Acad Press, New York, 1972; and "The Chemistry of Phosphorus," J. Emsley, D. Hall, Harper and Row, London, 1976, p. 82.

EXAMPLE 1

Preparation of
Tetrachloro-bis(aminophenoxy)cyclotriphosphazene

Sodium hydride (4.0 g of 60% oil dispersion, 0.1 mole) was slowly added at room temperature to p-aminophenol (10.9 g, 0.1 mole) in 75 ml tetrahydrofuran (THF), with stirring, under nitrogen. An exothermic reaction occurred and the reddish suspension became dark purple. Stirring was continued for at least one hour. The sodium aminophenolate suspension was then added dropwise over 0.5 hr. to a solution of hexachlorocyclotriphosphazene (17.4 g, 0.05 mole) in 100 ml THF. An off-white precipitate formed in the brown solution during the exothermic reaction. The reaction was allowed to continue for 24 hours. The mixture was then added to $H_2O$ (200 ml) with stirring, and the organic materials extracted with chloroform. The chloroform solution was dried over magnesium sulfate, filtered, and the solvent evaporated at room temperature under vacuum. A red/brown solid was obtained in 90–100% yield.

The product was analyzed by thin-layer chromatography. Aluminum oxide precoated sheets were used, as was an acetone/hexane 1:1 solvent. The resulting chromatograms were developed in an iodine chamber. The chromatograms obtained showed the product to contain tetrachloro-bis(aminophenoxy)cyclotriphosphazene.

EXAMPLE 2

Preparation of
Tetrachloro-bis(aminophenoxy)cyclotriphosphazene

The same procedure was carried out as in Example 1, except that the final reaction mixture was filtered, and the residue washed with THF. The filtrate solution was then evaporated at room temperature under vacuum, giving the solid product.

The weight of the washed off-white filtered residue was 5.8 g, which was the expected weight of NaCl formed in the reaction. This solid was insoluble in acetone or THF, but dissolved completely in water.

Thin-layer chromatographic analysis of the filtered THF solution (precoated alumina sheets were used; mobile phase: hexane/acetone 1:1) revealed the presence of two products which were deemed to be the cis and trans isomers of tetrachloro-bis(aminophenoxy)cyclotriphosphazene.

EXAMPLE 3

Preparation of
Tetrachloro-bis(aminophenoxy)cyclotriphosphazene

The same procedure was carried out as in Example 1, using the following reagent quantities: sodium hydride (60%), 2.0 g (0.05 mole); p-aminophenol, 5.45 g (0.05 mole); hexachlorocyclotriphosphazene, 8.7 g (0.025 mole).

Thin layer chromatography (precoated alumina sheets; methylene chloride as mobile phase) indicated two major products, and one minor. Very faint traces of unreacted hexachlorocyclotriphosphazene and p-aminophenol were also discernible.

EXAMPLE 4

Preparation of
Trichloro-tris(aminophenoxy)phosphazene

The same procedure as in Example 1 was followed with the appropriate change in reagent quantities: 60% sodium hydride, 3.0 g (0.075 mole); p-aminophenol, 8.18 g (0.075 mole); hexachlorocyclotriphosphazene, 8.7 g (0.025 mole). The product was a red/brown solid.

EXAMPLE 5

Preparation of
Pentachloro-mono(aminophenoxy)cyclotriphosphazene

The procedure as in Example 1 was used, except that the reagents used were: 100% sodium hydride, 2.4 g (0.1 mole) p-aminophenol, 10.9 g (0.1 mole); hexachlorocyclotriphosphazene, 34.5 g (0.1 mole). The product was isolated as a yellow oil, after THF evaporation.

EXAMPLE 6

Preparation of
Tetraphenoxy-bis(aminophenoxy)cyclotriphosphazene

A reaction solution of tetrachloro-bis(aminophenoxy)-phosphazene was prepared as in Example 1, except that the time of reaction of aminophenoxide salt and hexachlorocyclotriphosphazene was 8–10 hours. In a separate flask, phenol (18.8 g, 0.2 mole) was dissolved in 150 ml THF, and 100% sodium hydride (4.8 g, 0.2 mole) added slowly over 0.5 hour. This reaction was allowed to proceed until evolution of hydrogen was not visible. The resultant clear yellow solution of sodium phenoxide was slowly poured into the reaction mixture containing about 0.5 mole of tetrachloro-bis(aminophenoxy)phosphazene, and the combined mixture was heated at 60°–67° C. for about 3 days. The mixture was filtered, and the solvent evaporated at reduced pressure to give an amber oil. The infrared spectrum of this oil was identical to that obtained for the same compound prepared by a different method, as detailed in the prior cited D. Kumar, Journal of Polymer Science.

EXAMPLE 7

Preparation of Triphenoxy-tris(aminophenoxy)cyclotriphosphazene

The procedure of Example 6 was used, with a sample of trichloro-tris(aminophenoxy)cyclotriphosphazene, prepared as in Example 4, as the starting phosphazene reagent. The reagent amounts were: hexachlorocyclotriphosphazene, 0.05 mole; phenol, 0.21 mole; sodium hydride, 0.22 mole. The product was isolated as an amber oil, which contained traces of THF.

EXAMPLE 8

Preparation of a Polystyrene Blend 5 pph of $N_3P_3(OArNH_2)_6$ was blended with STYRON 680 (which is polystyrene, manufactured by The Dow Chemical Company), and kneaded in a Brabender mixing bowl at 200° C. and 50 rpm for 30 minutes. The phosphazene blend showed a much less reduction in torque, molecular weight of the polymer, and 10% solution viscosity as compared to a blend of STYRON 680 and FR-651P (which is FR 6519: monochloropentabromo-cyclohexane, manufactured by The Dow Chemical Company), or HBCD (which is hexabromocyclododecane, manufactured by Great Lakes Corporation). These results indicated that less polymer degradation occurred with phosphazenes of this invention than with the FR-651P and HBCD.

TGA data on the blend of this invention also showed that initial degradation temperatures were high. For example, isothermal analysis gave 335° C. as 5% weight loss point for the blend, compared to 320° C. for pure polystyrene. Blends with FR-651P or HBCD gave initial degradation temperatures below 320° C. Furthermore, increasing phosphazene content gave increasing thermal stability, whereas increasing FR-651P or HBCD content gave decreasing thermal stability.

The products of Examples 1, 2, 4, 6 and 7 were subjected to infrared spectroscopy. Solids were analyzed as nujol mulls while liquids were smeared onto NaCl plates and analyzed as liquid films.

Tetrachloro-bis(aminophenoxy)cyclotriphosphazene (Examples 1 and 2) and trichloro-tris(aminophenoxy)-cyclotriphosphazene (Example 4) showed infrared absorptions at (wavenumbers): 3460 and 3340 ($NH_2$), 1630–1600 and 1500 (C=C), 1220–1170 (P=N, and Ar—O).

Tetraphenoxy-bis(aminophenoxy)cyclotriphosphazene (Example 6) and triphenoxy-tris(aminophenoxy)-cyclotriphosphazene (Example 7) showed similar IR spectra, with major absorptions at (wavenumbers): 3460, 3360, 3240 (N—H), 3060 (Ar—H), 1625, 1590, 1500 (C=C), 1260 (P=N), and 1170 (Ar—O). The spectrum of the triphenoxy-tris(aminophenoxy)cyclotriphosphazene was almost exactly the same as a spectrum of this compound prepared by the known procedure, as published in the Journal of Polymer Science, Polymer Chemistry Edition, Volume 22, pages 927–943 (1982), by D. Kumar et al.

NMR spectroscopy was used to analyze the products of Examples 1 and 2. The products showed two superimposed AB2 systems, A=PCl, B=PCl(OArNH₂), corresponding to expected cis and trans isomers.

One isomer gave chemical shifts A=−24.16 ppm, B=−15.67 ppm, the coupling constant, J, was 64.6 Hz (1.78 ppm), and the ratio of coupling constant to chemical shift difference, J/v, was 0.21. The appearance of the spectrum was exactly as expected for an AB2 system with this ratio, as described in the texts referenced above.

The other isomer gave A=−23.96 ppm, B=−15.89 ppm, J=61.7 Hz (1.70 ppm), J/v=0.21, appearance as expected.

The presence of impurities was evidenced by small peaks, which were not satellite peaks, occurring between −17 and −22 ppm, but only constituted less than 5% of the product mix.

EXAMPLE 9

Preparation of Hexa(aminophenoxy)cyclotriphosphazene p-Aminophenol (38.2 g, 0.35 mole) was slurried under nitrogen, with 250 mL THF. Sodium hydride (9.6 g, 0.4 mole) was added quite rapidly over 5 minutes, and the reaction heated at 60°–67° C. over 24 hours. A solution of hexachlorocyclotriphosphazene (17.3 g, 0.05 mole) in THF (150 mL) was slowly added dropwise, by means of a dropping funnel, to the hot slurry above, and the resulting reaction heated at 60°–67° C. for 96 hours.

A sample of the reaction mixture was analyzed by 31P NMR spectroscopy. The spectrum showed the presence of two compounds. The major resonance signal was an apparent singlet at −10.2 ppm, which could be interpreted as either an AB₂ or A₃ system, and which was attributed to the desired hexa(aminophenoxy)cyclotriphosphazene. The minor component showed resonances at −6→−10 ppm, and −21→−26 ppm, which were in an AB₂ pattern, corresponding to the chloride-containing intermediate, monochloropenta(aminophenoxy)cyclotriphosphazene. The relative ratio of hexa(aminophenoxy)- to penta(aminophenoxy)cyclotriphosphazene was 2:1. Since no other compounds were present, the yield was therefore 66%. The indication is that quantitative yields are possible with longer reaction time. No aminol phosphazene was formed, as evidenced by a proton-coupled spectrum, which showed no difference when compared to the decoupled spectrum above.

What is claimed:

1. A process for the production of aminophenoxycyclotriphosphazene of the formula, $$N_3P_3(R_1)_n(R_2)_{6-n}$$

wherein $R_1$ is an aminophenoxy radical of the formula,

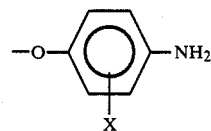

and $R_2$ has up to 6 carbon atoms and is an alkoxy, an alkenoxy, a fluoro-substituted alkoxy, a fluoro-substituted alkenoxy or an aryloxy radical of the formula,

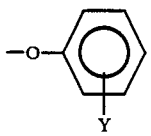

wherein each X is independently selected for each aminophenoxy radical from Cl, Br, F and H, each Y is independently selected for each aryloxy radical from Cl, Br, F and H, and wherein n is a whole integer which is $\geq 1$ and $\leq 6$ said process comprising, reacting a chlorocyclotriphosphazene and an $R_1$ salt to form an $R_1$-chlorocyclotriphosphazene having n $R_1$ substituents and $6-n$ chloride constituents and then reacting the $R_1$-chlorocyclotriphosphazene and an $R_2$ salt for a time period sufficient to yield said aminophenoxycyclotriphosphazene, said reactions in both steps occurring in an inert, organic solvent medium, at a temperature within the range of from about 20° C. to about 150° C., and with a molar ratio of said $R_1$-chlorocyclotriphosphazene to the $R_2$ anion component of said $R_2$ salt of 1:b wherein $b > 5 - n$.

2. The process of claim 1 wherein said $R_2$ salt is an alkali metal salt.

3. The process of claim 1 wherein said $R_2$ salt is a sodium salt.

4. The process of claim 1 wherein $R_2$ is phenoxide.

5. The process of claim 1 wherein $R_2$ is isopropoxide.

6. The process of claim 1 wherein $R_2$ is 2,2,2-trifluoroethoxide.

7. The process of claim 1 wherein $R_2$ is 2,2,3,3,4,4,4-heptafluorobutoxide.

8. The process of claim 1 wherein said temperature is within the range of from about 50° C. to about 140° C.

9. The process of claim 1 wherein n is 2 or 3.

10. The process of claim 1 wherein $b \geq 6 - n$.

11. The process of claim 1 wherein $R_2$ is an aryloxy radical.

* * * * *